(12) United States Patent
Schoenbeck

(10) Patent No.: US 8,337,651 B2
(45) Date of Patent: Dec. 25, 2012

(54) METHOD OF MAKING A TEXTILE WEB FROM WHICH ELASTICALLY STRETCHABLE DIAPER CLOSURES CAN BE STAMPED

(75) Inventor: Marcus Schoenbeck, Versmold (DE)

(73) Assignee: Nordenia Deutschland Gronau GmbH, Gronau (DE)

( * ) Notice: Subject to any disclaimer, the term of this patent is extended or adjusted under 35 U.S.C. 154(b) by 17 days.

(21) Appl. No.: 12/972,857

(22) Filed: Dec. 20, 2010

(65) Prior Publication Data

US 2012/0152435 A1    Jun. 21, 2012

(30) Foreign Application Priority Data

Dec. 29, 2009 (EP) .................................... 09016075

(51) Int. Cl.
*B32B 37/02* (2006.01)

(52) U.S. Cl. ........ 156/199; 156/166; 156/164; 156/157; 24/448; 428/99; 428/100

(58) Field of Classification Search ................ 156/199, 156/166, 164, 157, 229, 292, 297, 301, 302; 24/306, 445, 447, 448; 428/99, 110
See application file for complete search history.

(56) References Cited

U.S. PATENT DOCUMENTS

| | | | | |
|---|---|---|---|---|
| 5,389,168 A | * | 2/1995 | Litchholt et al. ................ | 156/77 |
| 5,468,321 A | * | 11/1995 | van Liempt et al. ........... | 156/159 |
| 5,702,551 A | * | 12/1997 | Huber et al. .................. | 156/73.1 |
| 5,763,041 A | * | 6/1998 | Leak et al. .................... | 428/100 |
| 5,830,298 A | * | 11/1998 | Jackson ......................... | 156/66 |
| 5,997,981 A | * | 12/1999 | McCormack et al. .......... | 428/99 |
| 6,527,028 B2 | * | 3/2003 | Miller ............................ | 156/555 |
| 6,547,909 B1 | * | 4/2003 | Butterworth ................... | 156/157 |
| 6,910,353 B2 | * | 6/2005 | Sasser et al. .................... | 66/191 |
| 7,032,278 B2 | * | 4/2006 | Kurtz, Jr. ....................... | 24/442 |
| 7,037,457 B2 | * | 5/2006 | Seidel et al. .................. | 264/267 |
| 7,850,809 B2 | * | 12/2010 | Schneider et al. ............ | 156/161 |
| 2002/0074079 A1 | * | 6/2002 | Reynolds et al. ............. | 156/164 |
| 2003/0173015 A1 | * | 9/2003 | Hamulski et al. ............ | 156/73.1 |
| 2004/0019343 A1 | * | 1/2004 | Olson et al. .............. | 604/385.24 |
| 2004/0076793 A1 | * | 4/2004 | Clune et al. .................. | 428/100 |
| 2004/0102754 A1 | * | 5/2004 | Morman et al. ......... | 604/385.24 |

(Continued)

FOREIGN PATENT DOCUMENTS

DE    102004035649 A    3/2006

*Primary Examiner* — Matthew Daniels
*Assistant Examiner* — Vishal I Patel
(74) *Attorney, Agent, or Firm* — Andrew Wilford

(57) ABSTRACT

A textile web from which elastically stretchable diaper closures can be stamped is made by first passing a pair of nonwoven textile webs longitudinally through a first laminating station at a predetermined first speed and inserting a plurality of longitudinally extending and transversely spaced strips of an elastic polymer between the webs at the first laminating station. This laminates the webs and strips together into an intermediate laminate having longitudinally extending zones where the webs are directly laminated to each other alternating with longitudinally extending stretch zones where the elastic strips are laminated between the webs. This intermediate laminate then passes through a second lamination station downstream of the first lamination station at a predetermined second speed smaller than the first predetermined speed. In the second lamination station respective inelastic strips are adhered to opposite faces of the intermediate laminate in the zones between the stretch zones.

7 Claims, 3 Drawing Sheets

U.S. PATENT DOCUMENTS

| | | | |
|---|---|---|---|
| 2006/0141884 A1* | 6/2006 | Haque | 442/361 |
| 2006/0162843 A1* | 7/2006 | Baldauf et al. | 156/73.1 |
| 2006/0182927 A1* | 8/2006 | Baldauf | 428/99 |
| 2006/0224137 A1* | 10/2006 | McCabe et al. | 604/385.22 |
| 2008/0081147 A1* | 4/2008 | Lindsay et al. | 428/100 |
| 2010/0291341 A1* | 11/2010 | Lester et al. | 428/99 |

* cited by examiner

METHOD OF MAKING A TEXTILE WEB FROM WHICH ELASTICALLY STRETCHABLE DIAPER CLOSURES CAN BE STAMPED

FIELD OF THE INVENTION

The present invention relates to a method of making a textile web. More particularly this invention concerns a textile web from which diaper closures can be stamped.

BACKGROUND OF THE INVENTION

A textile web from which elastically stretchable closures can be stamped has base layers each consisting of a nonwoven textile, as well as an elastic strip that is laminated between the base layers that forms an elastically stretchable section of the diaper closure. The base layers are wider in the direction of stretch than the laminated elastic strip and are connected with each other at overlapping attachment ends that are therefore not significantly elastic. One of the inelastic attachment ends of each closure is used for fastening to a diaper, and the other inelastic attachment end for attaching a fastener. A fastener can be in particular a patch with hooks or loops that forms part of a hook-and-loop fastener assembly.

From DE 10 2004 035 042, diaper closures are known with the described characteristics, as well as a method for the production of a textile web from which the described closures can be cut by stamping. The diaper closures can be formed as strips or can have the form of so-called elastic ears that are each wider at the attachment end attached to the diaper than at the opposite attachment end carrying the fastener. Large forces are transmitted by the fastener of a hook-and-loop fastener assembly to the diaper closure. For even transmission of force to the diaper fastener, the attachment ends must be resistant to bending and withstand as high a tensile strength as possible. In relation to their attachment ends, the known diaper closures are still in need of improvement.

OBJECTS OF THE INVENTION

It is therefore an object of the present invention to provide an improved method of making a textile web from which elastically stretchable diaper closures can be stamped.

Another object is the provision of such an improved method of making a textile web from which elastically stretchable diaper closures can be stamped that overcomes the above-given disadvantages, in particular that has attachment that are resistant to bending and have high tensile strength for a fastener or attachment.

Furthermore the web according to the invention should further be produced as economically as possible.

SUMMARY OF THE INVENTION

A textile web from which elastically stretchable diaper closures can be stamped is made by first passing a pair of nonwoven textile webs in a longitudinal direction through a first laminating station at a predetermined first speed and inserting a plurality of longitudinally extending and transversely spaced strips of an elastic polymer between the webs at the first laminating station. This laminates the webs and strips together into an intermediate laminate having longitudinally extending zones where the webs are directly laminated to each other alternating with longitudinally extending stretch zones where the elastic strips are laminated between the webs. This intermediate laminate then passes through a second lamination station downstream of the first lamination station at a predetermined second speed smaller than the first predetermined speed. In the second lamination station respective inelastic strips are adhered to opposite faces of the intermediate laminate in the zones between the stretch zones.

The method in accordance with the invention is a two-step lamination process. In a first step of the lamination process, a textile web is created that consists of nonwoven layers and laminated elastic strip that has, parallel to the web direction, alternating elastically stretchable zones and inelastic zones consisting of the nonwoven textiles bonded directly to each other. The textile web is not homogeneous and with respect to the layer thickness, as well as with respect to stretch properties. Due to the alternation of elastic and less elastic sections, the problem is created that parallel to the web direction, distortions can form in the textile web. The method is to be guided in such a way that the textile web can be fed to the second lamination station as a flat web without warping or distortion, in which condition the inelastic material strips are laminated onto the outside of the laminate. An important contribution to the solution of this problem is made by the characteristic that the longitudinal web-travel speed with which the laminate passes through the second lamination station is controlled in such a way that this longitudinal web-travel speed is always lower than the speed with which the textile web consisting of nonwovens and the elastic strips is brought together into the first lamination station during laminate formation. In this way, the web tension is reduced such that the textile web can be fed to the second lamination station without warping or waviness. Within the scope of the method in accordance with the invention, expensive measurements of the web tension are not required. In particular, the expensive regulation of web tension is eliminated when the longitudinal web-travel speeds are coordinated with each other according to the invention.

The longitudinal web-travel speed in the second lamination station and the speed with which the textile web consisting of nonwovens and the elastic strips is brought together in the first lamination station are advantageously set in such that they have a specified constant relationship. The relationship can be determined empirically, the values being advantageously set in such a way that the longitudinal web-travel speed in the second lamination station deviates by 0.1% to 1.0% from the speed at which the textile webs consisting of nonwovens and the elastic strips are merged in the first lamination station.

Advantageously, in the second lamination station, strips of nonwovens or elastic strips consisting of a inelastic polymer are laminated onto a first face of the laminate as reinforcement. In addition, in a second lamination station, bands with fasteners can also be laminated onto the second or opposite face.

The inelastic material strips laminated onto outer faces of the laminate are advantageously wider than the web zones between the elastic strips so that overlaps with the elastic zones result at the edges. The overlap section can, for example, be 2 mm to 10 mm wide and contribute to an even transmission of force between the reinforced connection section and the adjacent elastically stretchable section of the diaper closures stamped from the textile web.

For the production of the laminate produced in the first lamination station and for laminating on the inelastic material strip in the second lamination station, hot-melt adhesives can be used.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
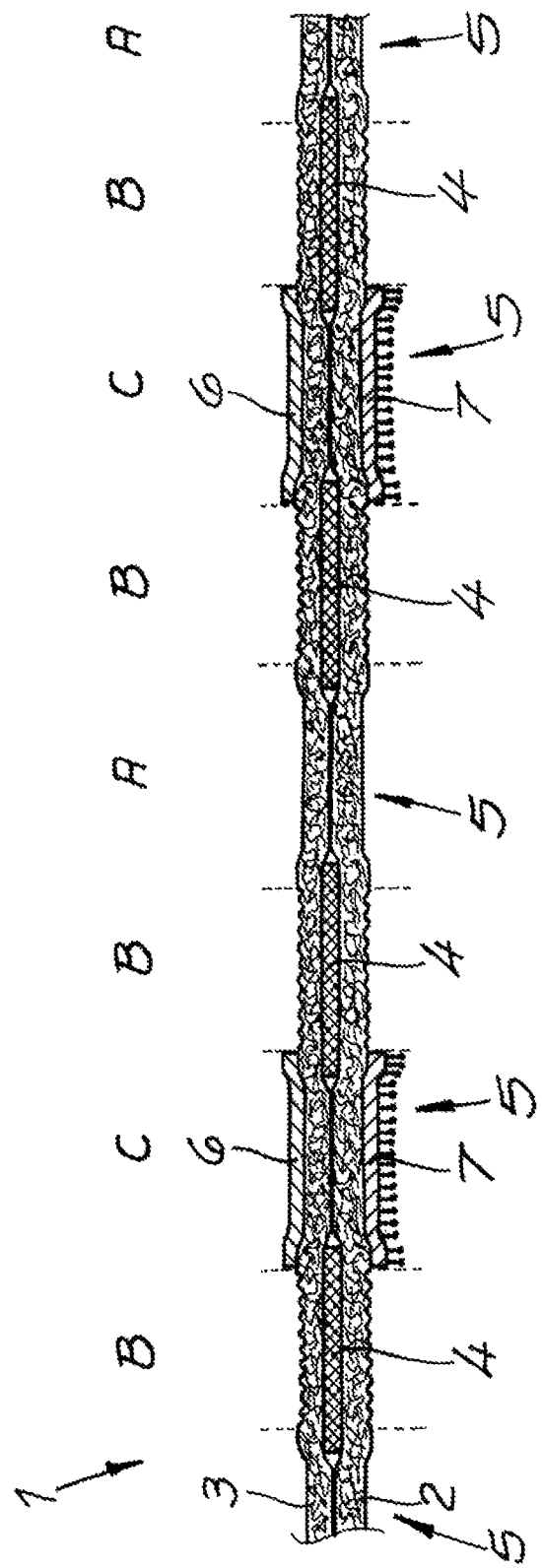
FIG. 1 is a cross section through a textile web from which a diaper fastener can be stamped.

As seen in FIG. 1 shows a cross section through a web 1 of material transverse to its longitudinal extent. The web 1 has two relatively inelastic outer base layers 2 and 3 of nonwoven textile sandwiching a plurality of longitudinally extending and transversely spaced elastic strips 4 of an elastically stretchable polymer film. In longitudinally extending web bands 5 formed between the elastic strips 4, the inelastic nonwoven base layers 2 and 3 are adhered together so that the longitudinally extending bands 5 are relatively inelastic.

A plurality of longitudinally extending and transversely spaced reinforcement strips 6 made of a nonwoven or an inelastic polymer are laminated onto the outer face of the base layer 3 on every other one of the bands 5 with the longitudinal edges of the strips 6 slightly transversely overlapping the longitudinal edges of the flanking elastic strips 4. Strips 7 carrying or forming fasteners, here hooks or loops, are laminated on the other base layer 2 directly opposite each of the strips 6 and with their longitudinal edges overlapping the edges of the flanking elastic strips 4, so that the strips 6 and 7 are of the same transverse width.

Figure 2:
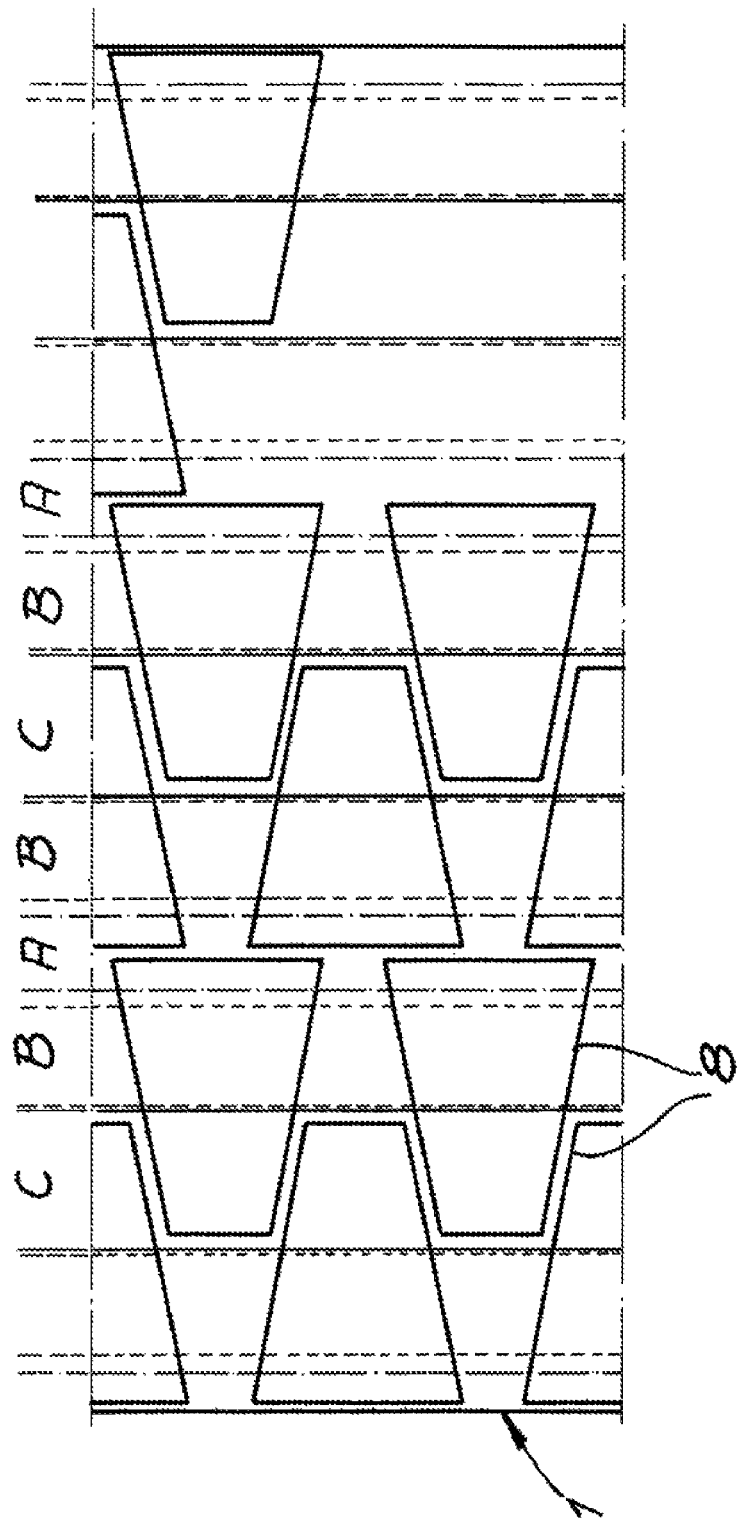
FIG. 2 is a top view illustrating the web.

The result as shown in FIG. 2 is a multilayer textile web 1 having a multiply repeating sequence of three zones A, B, and C that extend longitudinally. In the first zone A the nonwoven base layers 2 and 3 are directly bonded together. The zones B are elastically stretchable and have the base layers 2 and 3 sandwiching the elastic strips 4. The zones C consist of adhered together nonwoven layers 2 and 3, as well as inelastic material strips 6, 7 that have been laminated onto the outside of the laminate and reinforcement strips consisting of a inelastic polymer and/or form bands with fasteners. Diaper closures 8 can be stamped from the textile web 1, the contour of which was shown in FIG. 2 for illustration. The diaper closures 8 are, for example, so-called elastic ears with attachments ends one of which serves for connection to the diaper and is longer in the machine direction of the textile web 1 that the other that is secured to a fastener.

Figure 3:
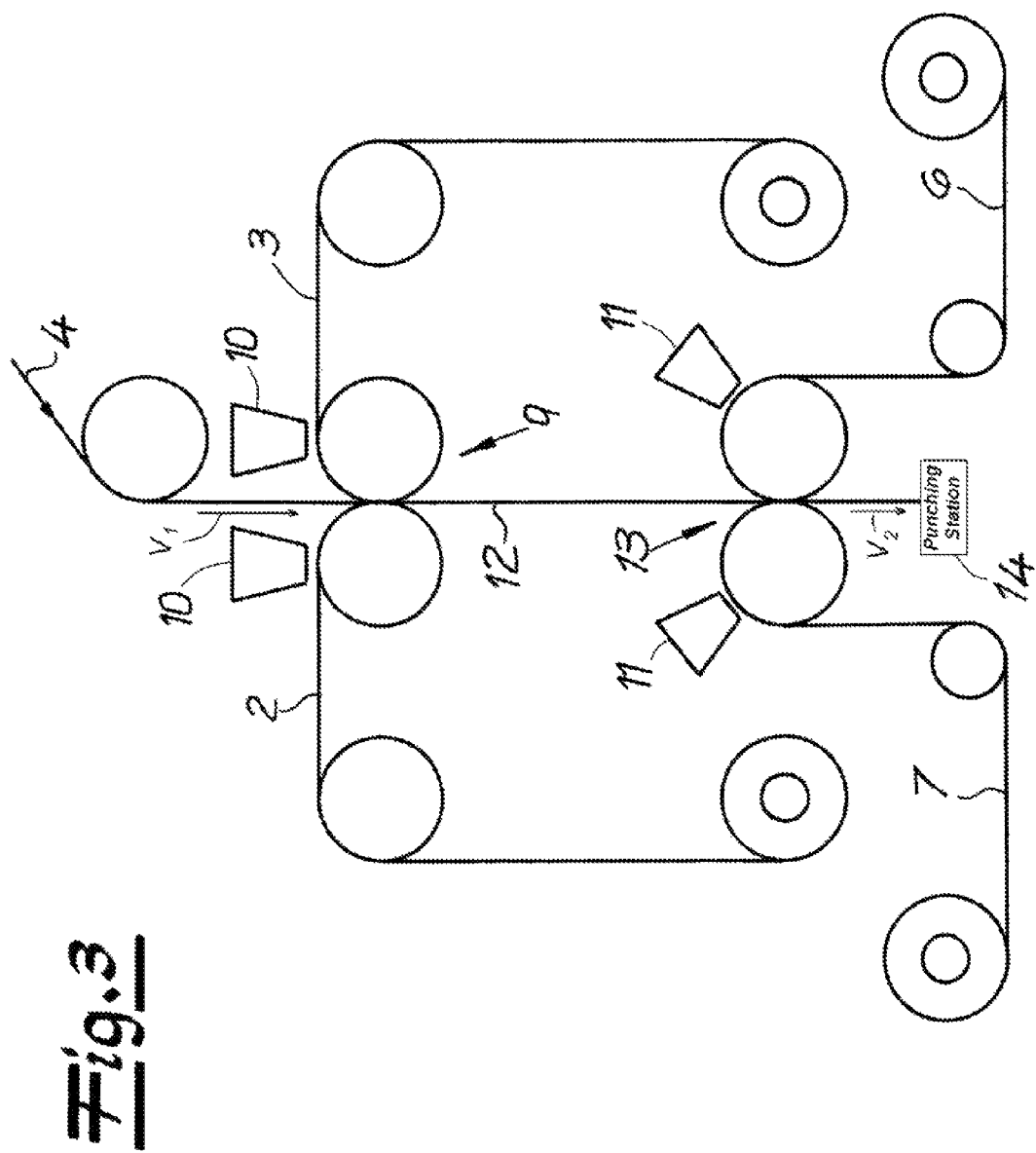
FIG. 3 is a schematic view showing how the web is made.

The method of making the described textile web is shown in FIG. 3. In a first lamination station 9, parallel elastic strips 4 transversely spaced from each other and each consisting of an elastically stretchable polymer are laminated between two relatively inelastic textile webs 2 and 3 made of a nonwoven to form the zones B, and alternate bands 5 between the elastic strips 4 are adhered directly together to form what will become the zones A and C of an intermediate laminate 12. This laminate 12 is fed to a second lamination station 13 where the inelastic material strips 6 and 7 with high tensile strength are laminated onto the outside of the laminate 12 at alternate bands 5, defining the zones C.

A longitudinal web-travel speed $V_1$ with which the intermediate laminate 12 passes through the second lamination station 13 is controlled, in accordance with the invention in such a way that this longitudinal web-travel speed is always less than the travel speed $V_2$ with which the textile web 10, 11 consisting of nonwovens and the elastic strips 4 are merged in the first lamination station 9 during the laminate formation. The longitudinal web-travel speed $V_2$ in the second lamination station 13 and the longitudinal web-travel speed $V_1$ in the first lamination station 9 have a specified constant relationship. The relationship is preferably selected in such a way that the longitudinal web-travel speed $V_2$ of the second lamination station 13 deviates by 0.1% to 1.0% from the speed $V_1$ at which the webs 2 and 3 are laminated with the elastic strips 4 in the first lamination station 9. Due to the coordination of the longitudinal web-travel speeds $V_1$ and $V_2$ as described, the web tension prior to the second lamination station 13 can be reduced to such a degree that no waviness and no warping occurs in the textile web 1.

For producing laminate 12 in the first lamination station 9, and for laminating on the inelastic material strip 6, 7 in the second lamination station 13, hot-melt adhesives are sprayed by applicators 10 and 11 in the stations 9 and 13, which are applied in adhesive stations.

In addition a punching station 14 is provided downstream of the second station 13 so that the isosceles-trapezoidal fasteners 8 (FIG. 2) can be punched from the finished laminate.

I claim:

1. A method of making a textile web from which elastically stretchable diaper closures can be stamped, the method comprising the steps of:
    passing a pair of nonwoven textile webs in a longitudinal direction through a first laminating station at a predetermined first speed;
    inserting a plurality of longitudinally extending and transversely spaced strips of an elastic polymer between the webs at the first laminating station such that the webs and strips are laminated together in the first station into an intermediate laminate having longitudinally extending zones where the webs are directly laminated to each other alternating with longitudinally extending stretch zones where the elastic strips are laminated between the webs;
    passing the intermediate laminate through a second lamination station downstream of the first lamination station at a predetermined second speed smaller than the first predetermined speed; and
    in the second lamination station adhering respective inelastic strips to opposite faces of the intermediate laminate in the zones between the stretch zones.

2. The method defined in claim 1 wherein one of the inelastic strips adhered to the intermediate laminate in the second station is an inelastic polymer or a nonwoven textile.

3. The method defined in claim 2 wherein the other of the inelastic strips carries a row of fasteners.

4. The method defined in claim 1 wherein the inelastic strips are broader than the respective zones between the flanking stretch zones and each overlap a part of each of the flanking stretch zones.

5. The method defined in claim 1 wherein a hot-melt adhesive is used to laminate the two webs to each other and to the elastic strips in the first station.

6. The method defined in claim 1 wherein the second speed bears a constant relationship to the first speed.

7. The method defined in claim 6 wherein the second speed is between 0.1% and 1.0% less than the first speed.

* * * * *